(12) United States Patent
Latimer et al.

(10) Patent No.: US 8,276,431 B1
(45) Date of Patent: Oct. 2, 2012

(54) METHOD OF DETERMINING ACOUSTIC TRANSIT TIMES FOR MATERIAL HAVING HIGH ACOUSTIC ATTENUATION PROPERTIES

(75) Inventors: Paul J. Latimer, Lynchburg, VA (US); Albert S. Birks, Corinth, MS (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 835 days.

(21) Appl. No.: 12/228,320

(22) Filed: Aug. 8, 2008

(51) Int. Cl.
*G01N 29/30* (2006.01)
*G01N 29/07* (2006.01)
(52) U.S. Cl. .............................. 73/1.86; 73/1.82; 73/597
(58) Field of Classification Search .................... 73/1.82, 73/1.86, 597, 598, 602
See application file for complete search history.

(56) References Cited

U.S. PATENT DOCUMENTS

| 3,423,993 | A | * | 1/1969 | Lynnworth | 73/639 |
|---|---|---|---|---|---|
| 4,435,984 | A | * | 3/1984 | Gruber | 73/628 |
| 4,437,332 | A | * | 3/1984 | Pittaro | 73/597 |
| 4,836,026 | A | * | 6/1989 | P'an et al. | 73/620 |
| 4,899,588 | A | | 2/1990 | Titlow et al. | |
| 5,115,673 | A | | 5/1992 | Kline et al. | |
| 5,127,268 | A | | 7/1992 | Kline | |
| 5,163,027 | A | * | 11/1992 | Miller et al. | 367/13 |
| 5,737,220 | A | | 4/1998 | Miller | |
| 6,047,600 | A | | 4/2000 | Ottosson et al. | |
| 6,116,080 | A | * | 9/2000 | Logue et al. | 73/24.05 |
| 6,534,964 | B1 | | 3/2003 | Sinha | |
| 6,810,743 | B2 | | 11/2004 | Madaras et al. | |
| 2005/0092091 | A1 | * | 5/2005 | Greelish | 73/617 |

* cited by examiner

*Primary Examiner* — Hezron E Williams
*Assistant Examiner* — Rose M Miller
(74) *Attorney, Agent, or Firm* — Fredric J. Zimmerman

(57) ABSTRACT

A method for determining time a single transit of an acoustic wave through a test material using a calibration material having known acoustic velocity characteristics and an acoustic pitch-catch system with a signal recorder for recording a received signal as a function of time. The system includes a first configuration for transmission of acoustic shear waves and a second configuration for transmission of acoustic longitudinal waves. In the first configuration, a first acoustic zero is determined when the acoustic shear waves are applied to the calibration material. In its second configuration, a second acoustic zero is determined when the acoustic longitudinal waves are applied to the calibration material. Each configuration is coupled to a test material with the respective first and second acoustic zeroes identified on the recorder. The signal recorder determines a single transit time for the acoustic waves through the test material.

16 Claims, 3 Drawing Sheets

METHOD OF DETERMINING ACOUSTIC TRANSIT TIMES FOR MATERIAL HAVING HIGH ACOUSTIC ATTENUATION PROPERTIES

ORIGIN OF THE INVENTION

The invention described herein was made in the performance of official duties by employees of the Department of the Navy and may be manufactured, used, licensed by or for the Government for any governmental purpose without payment of any royalties thereon.

FIELD OF THE INVENTION

The invention relates generally to non-destructive, acoustic testing of materials, and more particularly to a method of determining acoustic transit times for a material having high acoustic attenuation properties where the acoustic transit times can be used to calculate the velocity characteristics of the material.

BACKGROUND OF THE INVENTION

A conventional way of measuring an acoustic wave's time-of-flight through a material employs a "pitch-catch" system. Briefly, an acoustic pitch-catch system introduces an acoustic wave (e.g., an ultrasonic wave) into one side of a material and then detects the acoustic wave as it exits another side of the material. The time to transit the material may be used to determine various material characteristics such as the material's velocity characteristics, which are useful in calculating a material's elastic moduli. Typical pitch-catch systems utilize multiple transits of the acoustic wave (i.e., back and forth through the material) in order to minimize the effects of the time delay between the system's "electric zero" and "acoustic zero."

A system's electric zero is defined as the start time of the energy pulse used to generate the acoustic wave at the system's transmission transducer. However, system "electronics" (i.e., to include the energy pulse generator, wiring coupling the generator to the transmission transducer, and the transmission transducer itself) introduce a time delay such that the time that the acoustic wave is actually introduced into the material (i.e., the acoustic zero) is delayed relative to the time of the electric zero. The above-mentioned multiple transit approach is relatively effective when the material supports multiple transits of the acoustic wave as the effect of the time delay is spread out over the multiple transits. However, if the material under test is highly attenuating such that multiple transits of an acoustic wave are not supported, the error introduced by the time delay between a pitch-catch system's electric zero and acoustic zero can be significant.

SUMMARY OF THE INVENTION

Accordingly, it is an object of the present invention to provide a method of determining the time it takes for a single transit of an acoustic wave through a material.

Other objects and advantages of the present invention will become more obvious hereinafter in the specification and drawings.

In accordance with the present invention, a method is provided for determining the time for a single transit of an acoustic wave through a test material. The method includes the use of a block of a calibration material having known acoustic velocity characteristics. The block has a plurality of sections with each of the sections defining a known thickness. The method also uses an acoustic pitch-catch system that includes a signal recorder for recording a received signal as a function of time. The pitch-catch system has a first configuration for the transmission of acoustic shear waves and a second configuration for the transmission of acoustic longitudinal waves. In accordance with the method, a first acoustic zero for the pitch-catch system in its first configuration is determined when the acoustic shear waves are applied at normal incidence to each section of the block. Similarly, a second acoustic zero for the pitch-catch system in its second configuration is determined when the acoustic longitudinal waves are applied at normal incidence to each section of the block. Next, the pitch-catch system in its first configuration is coupled to a test material such that the acoustic shear waves can be applied at normal incidence to the test material. The first acoustic zero is identified on the signal recorder and is used to determine a single transit time for the acoustic shear waves to transit the test material. Next, the pitch-catch system in its second configuration is coupled to the test material such that the acoustic longitudinal waves can be applied at normal incidence to the test material. The second acoustic zero is identified on the signal recorder and is used to determine a single transit time for the acoustic longitudinal waves to transit the test material.

BRIEF DESCRIPTION OF THE DRAWINGS

Other objects, features and advantages of the present invention will become apparent upon reference to the following description of the exemplary embodiments and the drawings, wherein corresponding reference characters indicate corresponding parts throughout the several views of the drawings and wherein.

DETAILED DESCRIPTION OF EXEMPLARY EMBODIMENTS OF THE INVENTION

Figure 1:
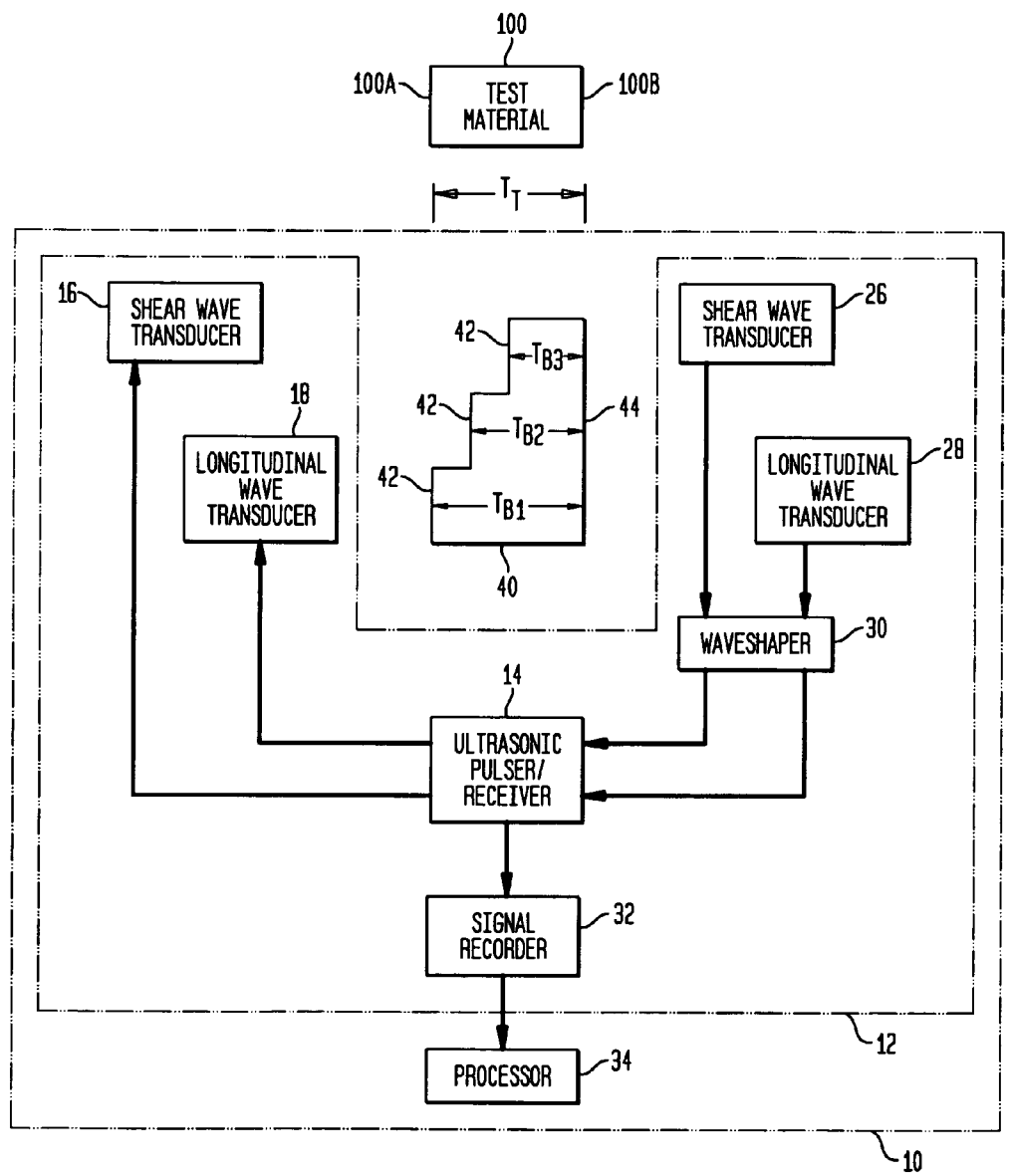
FIG. 1 is a schematic view of the test system used to determine the time it takes a single transit of an acoustic wave through a test material in accordance with the present invention.

Referring now to the drawings and more particularly to FIG. 1, a system that may be used to determine the time for a single transit of an acoustic wave through a test material 100 (i.e., between parallel end faces 100A and 100B) is shown within the dashed lines referenced by numeral 10. While test material 100 may be any material for which transit times must be determined, the present exemplary invention is particularly useful when test material 100 is a thick acoustically attenuating material that will only support a single transit of an acoustic wave therethrough. Such materials include, but are not limited to, non-metallic energetic materials. If a single transit through such a material can be accurately determined, the material's velocity and various elastic constants can be determined with precision in accordance with relationships known in the art.

At the heart of system 10 is an acoustic pitch-catch system 12 that can introduce acoustic waves into a material and detect/record when the acoustic waves exit the material. As is known in the art, pitch-catch system 12 includes an ultrasonic pulser/receiver 14 that can generate and receive electric pulses.

In general, the generated electric pulses are used by a transmission transducer to generate acoustic waves. In the present invention, two transmission transducers 16 and 18 are provided. Transducer 16 generates acoustic shear waves in response to electric pulses and transducer 18 generates acoustic longitudinal waves in response to electric pulses. While both transducers 16 and 18 are shown coupled to pulser/receiver 14, only one may be used/active at any given time. The reception side of pitch-catch system 12 uses a shear wave transducer 26 and a longitudinal wave transducer 28. The outputs of transducers 26 and 28 are provided to a waveshaper 30 to enhance the signal waveform prior to the transducer waveform being provided to pulser/receiver 14. While both transducers 26 and 28 are shown coupled to pulser/receiver 14, only one may be used/active at any given time.

The output of pulser/receiver 14 is provided to a signal recorder 32 that generally may generate a "signal versus time" display (e.g., video screen, printout, etc.) of the signals supplied thereto. The "signal versus time" data may also be provided to processor 34 for further processing.

The above-described elements of pitch-catch system 12 are well known in the art. Furthermore, the basic operation of pitch-catch system 12 is known and understood in the art. However, the present invention uses pitch-catch system 12 in a novel way to accurately establish/determine the time it takes for an acoustic wave to transit test material one time through its known thickness $T_T$. To do this, the present invention first determines the acoustic zero associated with pitch-catch system 12. That is, the present invention first calibrates pitch-catch system 12 to determine the time delay between the start of an electric pulse generated by pulser/receiver 14 and the start of the acoustic wave introduced into a material by one of transducers 16 and 18 when they receive the electric pulse. The time delay is caused by the electronics of pulser/receiver 14, the cabling coupling pulser/receiver 14 to either of transducers 16 and 18, and the electronics of transducers 16 and 18.

Figure 3:
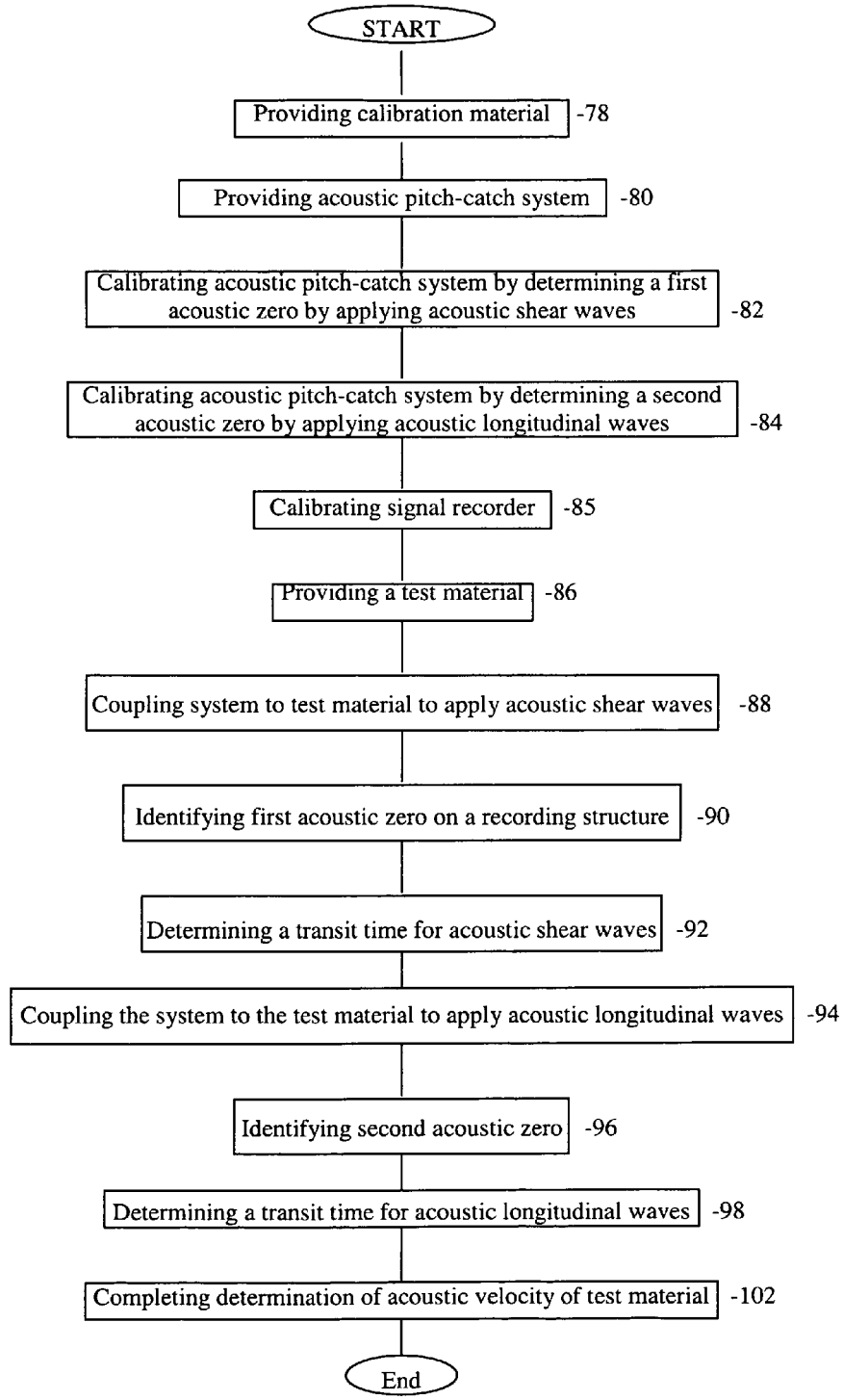
FIG. 3 is a flow chart depicting an exemplary method of determining acoustic transit times for material having high acoustic attenuation properties.

In accordance with the present invention, and as depicted in FIG. 3, the acoustic zero of pitch-catch system 12 is determined by using 78 a block 40 made from a material having well known acoustic velocity characteristics. More specifically, block 40 defines a number of steps 42 (e.g., three are shown although more could be used without departing from the scope of the present invention) on one side thereof and a flat face 44 on the other side thereof. For best measurement accuracy, the face of each step 42 should be parallel to flat face 44. The thickness of block 40 at each step 42 (e.g., $T_{B1}$, $T_{B2}$, and $T_{B3}$) is known precisely. While the use of a stepped block improves testing efficiency, individual blocks of unique and precisely known thickness could also be used.

To assure consistent acoustic velocity characteristics throughout block 40, the material used for block 40 should be isotropic and capable of supporting multiple transits of an acoustic wave therethrough. For example, block 40 could be made from aluminum as it is readily available and each to fabricate as block 40. However, any material (e.g., steel) having known acoustic velocity characteristics could also be used without departing from the scope of the present invention.

Pitch-catch system 12 is operated 80 to (i) apply 82 acoustic shear waves to each step 42 and measure the transit times associated therewith, and (ii) apply 84 acoustic longitudinal waves to each step 42 and measure the transit times associated therewith. More specifically, shear wave transducer 16 is coupled to a step 42 of block 40 while shear wave transducer 26 is coupled to flat face 44 of block 40 at a position that opposes transducer 16. Shear wave transducer 16 is coupled to block 40 such that the acoustic waves are applied at normal incidence to step 42. Pitch-catch system 12 is then operated to measure the transit times of the acoustic wave in block 40 between the two transducers. This process is repeated for each step 42 of block 40. The above-described process is then repeated using longitudinal wave transducers 18 and 28 with the longitudinal waves being applied to each step 42 at normal incidence. The measuring of such transit times using signal recorder 32 is well understood in the art.

The transit times from the above-described process in conjunction with the known velocity characteristics of block 40 and the known thickness thereof at steps 42 (e.g., $T_{B1}$, $T_{B2}$, and $T_{B3}$), provides for a precise determination of the start time for a single transit through block 40 at each step 42 (i.e., $t_{B1}$, $t_{B2}$, and $t_{B3}$) thereby accounting for delays inherent in the transducer and related electronics. The use of multiple steps 42 provides the redundancy needed to accurately determine the start time or acoustic zero.

Figure 2:
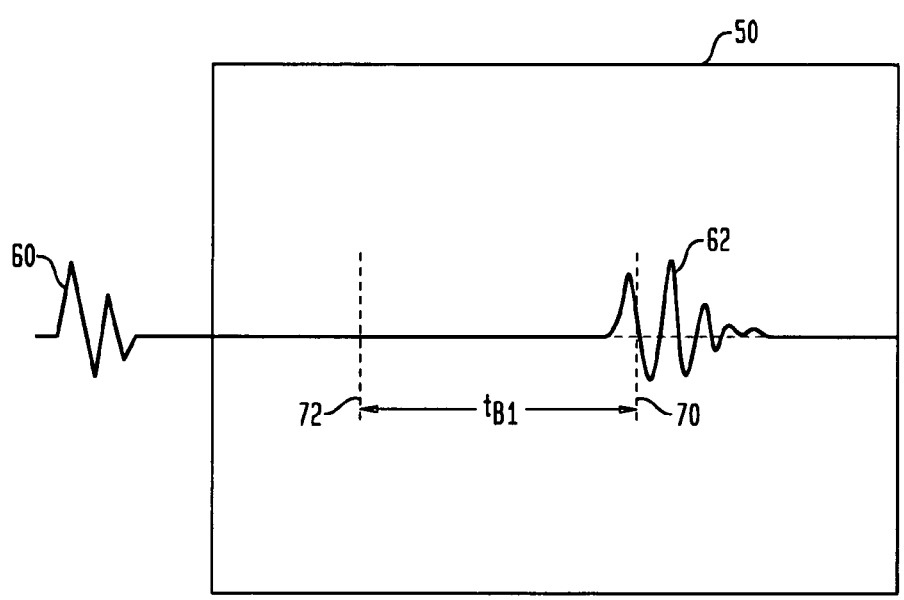
FIG. 2 is a graphic view illustrating the relationships between a pitch-catch system's electric pulse used to generate an acoustic wave, the acoustic zero for the pitch-catch system generating the acoustic wave based on the electric pulse as determined in accordance with the present invention, and the acoustic wave exiting a material after a single transit through the material.

The next step of the present invention involves using these transit times to calibrate 85 signal recorder 32. For example, if signal recorder 32 is a digital oscilloscope, the above-described application of pitch-catch system 12 to block 40 is repeated with the measured times $t_{B1}$, $t_{B2}$, and $t_{B3}$ being identified on the digital oscilloscope. When the digital oscilloscope displays a received acoustic wave, the measured single transit times are used to set a cursor of the digital oscilloscope at the acoustic zero for pitch catch system 12. This display is illustrated graphically in FIG. 2 where the digital oscilloscope's display is indicated by reference numeral 50.

By way of illustrative example, it will be assumed that shear wave transducers 16 and 26 are coupled to block 40 across thickness $T_{B1}$. In this case, pulser/receiver 14 generates an electric pulse 60 that is not recorded by the digital oscilloscope but is shown to provide a clear understanding of the present invention. Following a time delay introduced by pitch-catch system 12, electric pulse 60 causes an acoustic wave (not shown) to be introduced (by transducer 16) into block 40 such that an acoustic pulse 62 detected by transducer 26 will appear on display 50. Using the calculated single transit time $t_{B1}$ and the capabilities of the digital oscilloscope, the calculated single transit time $t_{B1}$ is used to "back up" from received acoustic pulse 62 to establish the acoustic zero for pitch-catch system 12. For example, one cursor (indicated by dashed line 70) is placed at the first downward zero crossing of received acoustic pulse 62. Note that any position of received acoustic pulse 62 may be used, but the first downward zero crossing provides a wave shape position that is easily recognized on an oscilloscope's trace. Furthermore, zero crossing points may be accurately located and readily replicated.

The calculated time $t_{B1}$ is then used to set a second cursor 72 of the digital oscilloscope. Specifically, cursor 72 is set backwards (in time) from cursor 70 by the single transit time $t_{B1}$.

Thus, cursor 72 sets the acoustic zero for pitch-catch system 12.

This process is repeated for all steps 42 of block 40 for both shear and longitudinal waves in order to establish an acoustic zero for the acoustic shear wave configuration of pitch-catch system 12 and an acoustic zero for the acoustic longitudinal wave configuration of pitch-catch system 12.

Once the acoustic zero for each configuration of pitch-catch system 12 is established, the single transit times for test material 100 are accurately determined for both acoustic shear and longitudinal waves by providing 86 the test material 100. For acoustic shear wave measurements, transducers 16 and 26 are coupled 88 to respective faces 100A and 100B of test material 100, and pitch-catch system 12 is operated using the digital oscilloscope 50 (configured with the cursor marking the acoustic zero) being used for signal recorder 32 to identify the first acoustic zero on a recording structure 90. Accordingly, a single transit time is determined 92 for the acoustic shear wave to transit the test material. Coupling 94 is performed in a second configuration of the test material so the acoustic longitudinal waves may be applied at, in an exemplary embodiment, a normal incidence to the test material 100. The second acoustic zero is identified 96 on the digital oscilloscope 50. For acoustic longitudinal wave measurements, transducers 16 and 26 are replaced with transducers 18 and 28 in order to determine 98 a single transit time for the acoustic longitudinal wave. With the single transit times accurately determined in accordance with the present invention and since the precise thickness $T_T$ is known, an accurate acoustic velocity of test material 100 is readily determined 102.

The acoustic velocity may be used in the calculations of a variety of elastic moduli whose relationships are well known and understood in the art.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

Finally, any numerical parameters set forth in the specification and attached claims are approximations (for example, by using the term "about") that may vary depending upon the desired properties sought to be obtained by the present invention.

At the very least, and not as an attempt to limit the application of the doctrine of equivalents to the scope of the claims, each numerical parameter should at least be construed in light of the number of significant digits and by applying ordinary rounding.

What is claimed as new and desired to be secured by Letters Patent of the United States is:

1. A method of determining the time for a single transit of an acoustic wave through a test material, comprising:
   providing a calibration material having known acoustic velocity characteristics, said calibration material having a plurality of sections with each of said sections defining a known thickness;
   providing an acoustic pitch-catch system that includes a recording structure for recording a received signal as a function of time, said pitch-catch system having a first configuration for the transmission of acoustic shear waves and a second configuration for the transmission of acoustic longitudinal waves;
   determining a first acoustic zero for said pitch-catch system in said first configuration when said acoustic shear waves are applied at normal incidence by said pitch-catch system to each of said sections of said block;
   determining a second acoustic zero for said pitch-catch system in said second configuration when said acoustic longitudinal waves are applied at normal incidence by said pitch-catch system to each of said sections of said calibration material;
   providing a test material of known thickness;
   coupling said pitch-catch system in said first configuration to the test material such that said acoustic shear waves can be applied at normal incidence to the test material;
   identifying said first acoustic zero on said recording structure;
   determining a single transit time for said acoustic shear waves to transit the test material using said pitch-catch system in said first configuration with said first acoustic zero so-identified;
   coupling said pitch-catch system in said second configuration to the test material such that said acoustic longitudinal waves can be applied at normal incidence to the test material;
   identifying said second acoustic zero on said recording structure; and
   determining a single transit time for said acoustic longitudinal waves to transit the test material using said pitch-catch system in said second configuration with said second acoustic zero so-identified.

2. The method according to claim 1, wherein said calibration material is a block of calibration material, and wherein said calibration material is comprised of an isotropic material.

3. The method according to claim 1, wherein said calibration material is a block of calibration material selected from the group consisting of aluminum and steel.

4. The method according to claim 1, wherein said calibration material is a stepped block of calibration material, and wherein each of said sections is defined by a step in said stepped block.

5. The method according to claim 1, wherein said recording structure comprises a digital oscilloscope.

6. The method according to claim 5, wherein said identifying said first acoustic zero comprises fixing a cursor of said digital oscilloscope at said first acoustic zero.

7. The method according to claim 5, wherein said identifying said second acoustic zero comprises fixing a cursor of said digital oscilloscope at said second acoustic zero.

8. A method of determining the time for a single transit of an acoustic wave through a test material, comprising:
   providing a stepped block of an isotropic material, said stepped block having a plurality of stepped sections with each of said stepped sections defining a known thickness;
   providing an acoustic pitch-catch system that includes recording structure for recording a received signal as a function of time, said pitch-catch system having a first configuration for the transmission of acoustic shear waves and a second configuration for the transmission of acoustic longitudinal waves;
   determining a first acoustic zero for said pitch-catch system in said first configuration when said acoustic shear waves are applied at normal incidence by said pitch-catch system to each of said stepped sections of said stepped block;
   determining a second acoustic zero for said pitch-catch system in said second configuration when said acoustic longitudinal waves are applied at normal incidence by said pitch-catch system to each of said stepped sections of said stepped block;
   providing a test material of known thickness;
   coupling said pitch-catch system in said first configuration to the test material such that said acoustic shear waves can be applied at normal incidence to the test material;
   identifying said first acoustic zero on said recording structure;

determining a single transit time for said acoustic shear waves to transit the test material using said pitch-catch system in said first configuration with said first acoustic zero so-identified;

coupling said pitch-catch system in said second configuration to the test material such that said acoustic longitudinal waves can be applied at normal incidence to the test material;

identifying said second acoustic zero on said recording structure; and determining a single transit time for said acoustic longitudinal waves to transit the test material using said pitch-catch system in said second configuration with said second acoustic zero so-identified.

9. The method according to claim 8, wherein said isotropic material is selected from the group consisting of aluminum and steel.

10. The method according to claim 8, wherein said recording structure comprises a digital oscilloscope.

11. The method according to claim 10, wherein said identifying said first acoustic zero comprises fixing a cursor of said digital oscilloscope at said first acoustic zero.

12. The method according to claim 10, wherein said identifying said second acoustic zero comprises fixing a cursor of said digital oscilloscope at said second acoustic zero.

13. A method of determining the time for a single transit of an acoustic wave through a test material, comprising:

providing a block of a calibration material having known acoustic velocity characteristics, said block having a plurality of sections with each of said sections defining a known thickness;

providing an acoustic pitch-catch system that includes a digital oscilloscope for recording a received signal as a function of time, said pitch-catch system having a first configuration for the transmission of acoustic shear waves and a second configuration for the transmission of acoustic longitudinal waves;

determining a first acoustic zero for said pitch-catch system in said first configuration when said acoustic shear waves are applied at normal incidence by said pitch-catch system to each of said sections of said block;

determining a second acoustic zero for said pitch-catch system in said second configuration when said acoustic longitudinal waves are applied at normal incidence by said pitch-catch system to each of said sections of said block;

providing a test material of known thickness;

coupling said pitch-catch system in said first configuration to the test material such that said acoustic shear waves can be applied at normal incidence to the test material;

identifying said first acoustic zero on said digital oscilloscope;

determining a single transit time for said acoustic shear waves to transit the test material using said pitch-catch system in said first configuration with said first acoustic zero so-identified;

coupling said pitch-catch system in said second configuration to the test material such that said acoustic longitudinal waves can be applied at normal incidence to the test material;

identifying said second acoustic zero on said digital oscilloscope; and determining a single transit time for said acoustic longitudinal waves to transit the test material using said pitch-catch system in said second configuration with said second acoustic zero so-identified.

14. The method according to claim 13, wherein said block of calibration material comprises an isotropic material.

15. The method according to claim 13, wherein said block of calibration material is selected from the group consisting of aluminum and steel.

16. The method according to claim 13, wherein said block of calibration material is a stepped block, and wherein each of said sections is defined by a step in said stepped block.

\* \* \* \* \*